United States Patent [19]

Haerr

[11] 4,159,719

[45] Jul. 3, 1979

[54] MOISTURE-EXPANDABLE EAR WICK

[75] Inventor: Raymond H. Haerr, Cincinnati, Ohio

[73] Assignee: Xomed, Inc., Cincinnati, Ohio

[21] Appl. No.: 794,917

[22] Filed: May 9, 1977

[51] Int. Cl.² .......................... A61F 1/18; A61M 31/00
[52] U.S. Cl. ..................................... 128/260; 128/151; 128/270
[58] Field of Search ............... 128/260, 261, 269, 270, 128/151, 152, 285, 263, 341, 296, 343, 267

[56] References Cited

U.S. PATENT DOCUMENTS

| | | | |
|---|---|---|---|
| 2,351,836 | 6/1944 | Popper | 128/263 |
| 2,804,072 | 8/1957 | Genzer | 128/152 |
| 2,968,858 | 1/1961 | Brenner et al. | 128/296 X |
| 3,674,030 | 7/1972 | Jones et al. | 128/285 |

FOREIGN PATENT DOCUMENTS

| | | | |
|---|---|---|---|
| 490024 | 8/1938 | United Kingdom | 128/270 |
| 1204117 | 9/1970 | United Kingdom. | |
| 1306029 | 2/1973 | United Kingdom. | |

*Primary Examiner*—Henry J. Recla
*Attorney, Agent, or Firm*—John G. Schenk

[57] ABSTRACT

A tightly coiled, substantially cylindrical wick of compressed, dehydrated, sponge-like material having sufficient rigidity to be inserted endwise into an ear canal will, when hydrated, uncoil and expand radially whereby to substantially engage the inner surface of the ear canal for applying medicament to said inner surface while securing it against accidental or unintentional dislodgment therefrom. When hydrated, a central opening is provided through the uncoiled member through which opening sound waves may freely pass en route to the ear drum.

10 Claims, 10 Drawing Figures

MOISTURE-EXPANDABLE EAR WICK

BACKGROUND OF THE INVENTION

1. Field of the Invention

The invention relates to a dehydrated wick of tightly coiled, cellular, sponge-like material which possesses sufficient rigidity to enable it to be inserted endwise into an ear canal without distortion or bending, and which when so positioned and hydrated, will uncurl and expand whereby to snugly engage the inner peripheral walls of the ear canal.

This invention is a modification of the moisture-expandable prosthesis of my U.S. Patent application Ser. No. 608,148, now U.S. Pat. No. 4,034,759.

The primary distinction between the wick of this application and the prosthesis of my aforesaid patent, resides in the structural details of the wicks per se. The wick of this application comprises a tightly coiled length of compressed, dehydrated, expandable, soft, cellular material which, if hydrated while unrestrained, will expand to its original, uncurled, flat, precompressed thickness.

The prosthesis of my patent comprises an elongate, hollow, dehydrated, tubular member of soft cellular material which has been radially compressed whereby the opening through the tubular member is closed and wherein said member assumes a minimum outer dimension.

When the wick of the present invention is hydrated, it literally uncoils like a spring until the outer surface of the uncoiling member, engages the inner surface of an ear canal, or the like. As the wick uncoils an opening is provided interiorly of and throughout the length of the wick.

In sharp contrast thereto, the wick of my patent, when hydrated, expands radially, and if unrestrained it will reassume the elongate, hollow, tubular shape that it had before it was dehydrated and radially compressed.

2. Description of the Prior Art

Applicant is aware of a recent advertisement of the Mentor Division of Codman & Shurtleff, Inc. of Randolph, Maine, of an ear wick developed by John S. Taylor, M.D. as per the photocopy which is attached to and comprises part of this application.

It is applicant's understanding that the Taylor Ear Wick is made by compressing a thick sheet of suitable cellular material to a minimum thickness after which the compressed sheet is cut into individual wicks of a predetermined length, each wick being substantially square in cross section. When moistened the Taylor Ear Wick expands in a lateral plane only, forming a sheath which traces and encircles the wall of "the outer ear canal." The ultimate length of the fully expanded wick approximates the thickness of the sheet from which the wick was cut prior to its initial compression.

The Stephan U.S. Pat. No. 1,210,720, dated Jan. 2, 1917, discloses a surgical cotton splint fabricated into a substantially projectile-shaped member by feeding one or more laminae absorbent cotton to a rewind spindle and placing the cotton toward the axis or along the spindle and beyond the point thereof as the cotton winds upon itself. Each of the cotton layers becomes so immeshed with the adjacent layer that there is no possibility of the finished product unwinding. By reason of the thinness of the successive layers, the resulting product is a homogenous body of compacted cotton fiber arranged about a center in an elongated pointed form and having sufficient stiffness to be utilized without a handle for use by surgeons, oculists, and nurses for the cleaning of nostrils, ears, etc. The aforesaid splint is not adapted to expand or swell when subjected to moisture.

Applicant is also aware of the following U.S. patents:

Strauss U.S. Pat. No. 2,490,168 which discloses a sinus medication applicator which comprises an elongate, hollow stem having a plurality of lateral openings in open communication with a porous or spongy body member secured to and carried by the stem;

Pietro U.S. Pat. No. 3,506,009, which is directed to a method of making styptic-tipped medical sticks;

Brillant U.S. Pat. No. 3,018,778, which discloses a pellet fabricated from material which expands when it is wet and becomes soft so as to yield and become distorted under light pressure, either to fill or to reach all surfaces of a cavity, or to provide a larger wiping surface and to provide more intimate contact with the surface to be dried or treated, wherein the pellet is fabricated from "sponge rubber," and wherein the pellet is secured to and carried by a thin, flexible applicator of wood, metal or plastic;

Strauss U.S. Pat. No. 2,170,222, which discloses a sponge applicator which is secured to and carried by a hollow tube through which medicant, and other liquids, is supplied to the interior of the sponge;

Davis U.S. Pat. No. 2,510,961, which discloses an ear cleaner which includes a pad of soft, elastic, porous material having good cleansing and scrubbing qualities such as sponge or foam rubber;

Negri U.S. Pat. No. 2,642,065, which discloses a vial containing an analgesic fluid in a protecting container having a substantially fresto-conical shape, from one end of which an absorbent element projects for the purpose of spreading fluid inside of the auditory meatus;

Hartop U.S. Pat. No. 3,865,108, discloses a drug delivery device having a drug containing zone associated with and partially defined by a material which swells on contact with body fluids. When swelling occurs, the pressure on the drug containing zone expels the drug from the device.

Crockford U.S. Pat. No. 2,254,272, which discloses a solid tampon of viscose or cellulose sponge material.

Buryan U.S. Pat. No. 2,603,213, which discloses a post-operative bandage which is fabricated in such a manner as to minimize the discomfort normally encountered when a bandage for post-operative use following surgery in the anus or vagina is removed.

Jones, et al, U.S. Pat. No. 3,674,030, which discloses a catamenial tampon comprising an elongate, solid, strip of regenerated cellulose, sponge material.

Mullan U.S. Pat. No. 3,559,646, which discloses a tampon having a hollow body of compressible sponge-like, adsorptive and/or absorbent material which is closed at one end. The opening is adapted to receive a medicant capsule which is adapted to be broken releasing medication interiorly of the tampon.

British Pat. No. 1,306,029 dated Sept. 30, 1971 to Battelle Development Corporation discloses improvements in or relating to prefabricated auditory canal wick wherein an elongate, solid, cylindrical wick 18 is provided with an enlarged disc-like portion 14 which determines the amount by which the cylinder portion may be inserted into the ear canal. The tubular portion is fabricated from a relatively porous material which expands on contact with medicated liquid which it retains after expansion. When expanded, the ear canal is completely blocked.

British Pat. No. 1,343,284 dated Feb. 24, 1970 to the Viscoe Group, Ltd. discloses a solid catamenial tampon which is fabricated from regenerated cellulose sponge material which expands when moistened.

British Pat. No. 1,204,117 dated Sept. 8, 1969 to Syntex Corporation discloses devices and methods for administering pharmaceutical preparations to domestic animals by means of a substantially cylindrical-shaped tampon fabricated from resilient material and size whereby to be inserted into the ear canal of an animal, said tampon being provided with a suitable pharmaceutical coating.

British Pat. No. 578,613 dated Dec. 22, 1943 of Jacob Joseph Cantor discloses a device for protecting the ear drum which comprises an elongate, hollow, rubber shield having a closed forward end, and an open rearward end. Said sheath is adapted to be collapsed and inserted into an ear canal to the extent permitted by an upstanding diametrical projection or flange. After insertion, the collapsed sheath will assume a cylindrical shape which is adapted to be filled with a resilient sound-absorbing material. The device completely blocks the ear canal.

DESCRIPTION OF THE PREFERRED EMBODIMENT

Figure 1:
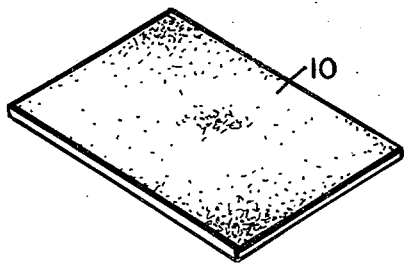
FIG. 1 is a perspective view of a flat, compressed sheet of cellular sponge-like material from which the ear wick is fabricated.

In FIG. 1 the numeral 10 represents a substantially rectangular sheet of compressed, dehydrated, soft, cellular material which when hydrated and unrestrained, will expand to its original flat, pre-compressed thickness.

Figure 2:
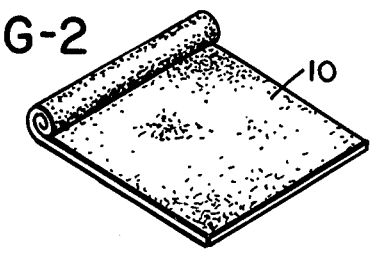
FIG. 2 is a perspective view of the sheet of FIG. 1 in the initial stage of being tightly coiled.
Figure 3:
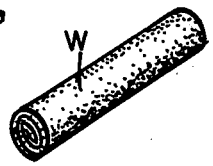
FIG. 3 is a view similar to FIG. 2 of the completed ear wick.

Such a sheet of compressed material measuring, by way of example, ⅜ inch wide by say 1" long and from 0.015 to 0.020 thick, is tightly coiled as illustrated in FIGS. 2 and 3 for providing an elongate tightly coiled wick W having an overall length equal to the original width of the sheet from which the coiled wick is fabricated.

Figure 4:
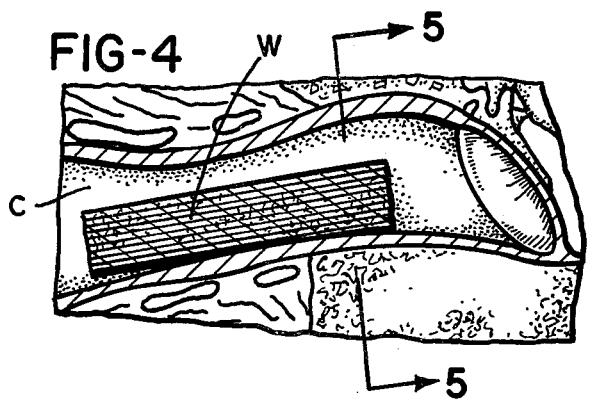
FIG. 4 is a fragmentary section view showing the ear wick of FIG. 3 inserted in an ear canal.
Figure 5:
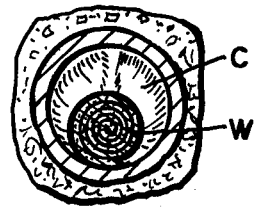
FIG. 5 is a view taken on line 5—5 of FIG. 4.

The individual convolusions of the coiled wick are, as illustrated in FIG. 3, tightly compressed, whereby the wick will be sufficiently rigid for endwise insertion into the ear canal C as in FIGS. 4 and 5 without distortion or bending. Having thus been inserted into an ear canal the tightly coiled wick will, when moistened by a liquid medicament, or the like, rapidly expand radially as it uncoils to the position and condition illustrated in FIGS. 6 and 7 wherein the outer surface of the expanded convolusion will snuggly and abuttingly engage the inner peripheral surfaces of the ear canal whereby the medicament which caused the hydration of the initially coiled wick will be disposed and maintained in contacting relationship with the inner surface of the ear canal.

Figure 6:
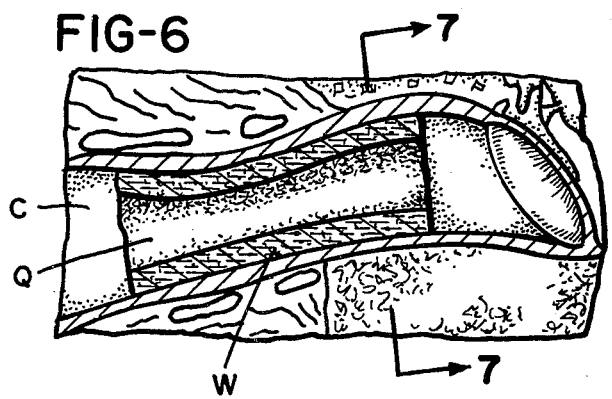
FIG. 6 is a view similar to FIG. 4 showing the wick after it has uncoiled due to hydration.
Figure 7:
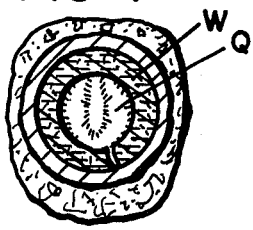
FIG. 7 is a view taken on line 7—7 of FIG. 6.
Figure 8:
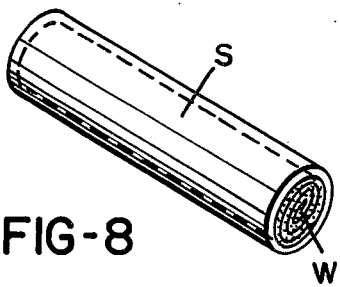
FIG. 8 is a perspective view of the wick of FIG. 3 completely housed within a protective sheath.

As clearly illustrated in FIGS. 6 and 7 the uncoiled, radially expanded wick includes a central opening Q which extends throughout the length of the wick, said opening permitting air and sound waves to readily pass through the interior of the wick whereby to reach the ear drum.

It should be noted that in the event the wick should be hydrated before being inserted into an ear canal, the expanding action of the material is such that it would uncoil to assume the initial flat position of FIG. 1.

In order to prevent the accidental and/or unintentional expansion of the tightly coiled wick of FIG. 3 said wick may be confined within a tubular protective sheath S of fairly rigid, thin wall, polyethylene or the like, which will effectively maintain the wick in a fully coiled, compact, dehydrated condition. Said sheath will in the event that the exposed ends of wick should be moistened, will prevent the wick from expanding and/or uncoiling.

Figures 9, 10:
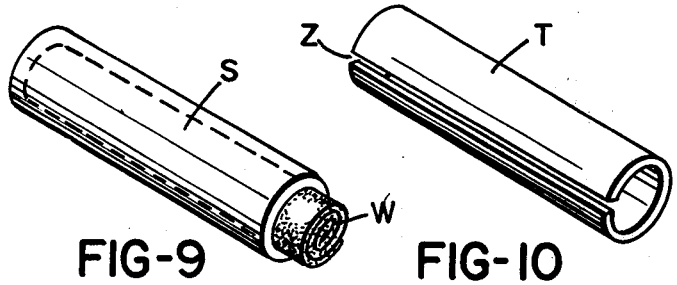
FIG. 9 is a view similar to FIG. 8 showing the wick in a protective sheath with one end of the wick protruding to facilitate its removal from the sheath.
FIG. 10 is a perspective view of a modification of the protective sheath of FIG. 8.

In FIG. 9 the protective sheath S is somewhat shorter than the overall length of wick W whereby a portion of one end of the wick will normally protrude beyond an end of the sheath for thereby providing an exposed end which can be readily grasped for facilitating the endwise withdrawal of the wick from the sheath.

In FIG. 10 I have illustrated a resilient split sheath T, the length of which may be equal to, greater, or less than the overall length of wick W. Sheath T, being longitudinally split at Q may be more easily associated with and removed from wick W, than sheath S.

Uniformly satisfactory results have been obtained in those instances in which sheet 10 is fabricated from a cellular material which comprises a fine pore regenerated cellulose sponge as manufactured by The O-Cell-O Division of General Mills from sulphite wood pulp, however, equally satisfactory results have been obtained in those instances in which the cellular material comprises a biocompatible polymer which is free of cellulose fibers and characterized by a multiplicity of fine pores, as produced by Americal Corporation of Mystic, Connecticut under the trademark "MEROCEL" which is described as a pure white synthetic fiber made by open cell polymerizing a biocompatible polymer carbohydrate and forming sheets of controlled pore size cell networks all welded at every crossover point to prevent any media migration. "MEROCEL" is characterized by a very high fluid holding capacity which results in initially fast capillary action with cell expansion and overall swelling. It should, of course, be understood that any other suitable cellular material which is capable of expanding when moistened from a compressed dehydrated state can be utilized.

What is claimed is:

1. An elongate, spirally wound, compressed moisture-expandable ear canal wick for applying medicament to the interior surface of an ear canal, the wick comprising an initially flat length of moisture-expandable dehydrated sponge-like material said material being coiled up and compressed into an elongate device which is insertable into an ear and has a pair of ends and an outside diameter of approximately 2 to 3 mm, said material being characterized in that when hydrated by a liquid medicament said material uncoils so that the outer surface of said elongate device engages the interior surface of an ear canal in which the device is inserted prior to hydration, said outer surface contacting an ear canal inner surface to apply medicament to the interior surface of the ear canal, said uncoiling causing said device to expand radially outward and defining an open, unobstructed passage through the wick, said passage extending longitudinally of said device for essentially the entire length thereof and connecting said device ends together and permitting substantially free unobstructed passage of sound waves through the wick from one end of said device to the other end thereof whereby a user's hearing is essentially unimpaired when said wick is positioned within said user's ear canal and expanded into contact with the inner surfaces of that ear canal, said material being characterized such that when hydrated while unconfined said device will expand and completely uncoil to its original flat, non-compressed dimensions.

2. A wick as called for in claim 1, wherein the material prior to coiling comprises a flat, compressed sheet which when tightly coiled, comprises an elongate, cylindrical, compact member which is sufficiently rigid for endwise insertion into an ear canal without distortion or bending.

3. A wick as called for in claim 1, wherein the sponge-like material is characterized by a multiplicity of fine pores.

4. A wick as called for in claim 1 further including a moisture-proof, cylindrical, elongate member for housing said wick.

5. A device as called for in claim 4 wherein said housing comprising an elongate tubular member, the inside diameter of which approximates the outside diameter of the dehydrated wick housed therein, said housing material precluding the accidental or unintentional expansion of said material, prior to, or after, hydration while confined within said housing.

6. A device as called for in claim 4, wherein one end of the wick within the housing projects outwardly beyond an end of said housing for defining a means engageable for removing the material from said housing.

7. A device as called for in claim 4, wherein the housing comprises a length of tubular material which has been longitudinally split whereby to yieldably engage the outer surface of the wick housed therein.

8. A wick as called for in claim 1, wherein said device outer surface contacts an ear inner surface over substantially the entire length of said device.

9. A method of applying a medicament to an interior surface of an ear canal over a prolonged period of time, comprising the steps of: forming a wick of compressed, dehydrated, hydro-expandable, sponge-like material of an initially flat length of moisture-expandable dehydrated sponge-like material, said material being coiled up and compressed into an elongate device which is insertable into an ear and has a pair of ends and an outside diameter of approximately 2 to 3 mm, said material being characterized in that when hydrated by a liquid medicament said material will uncoil so that the outer surface of said elongate device will engage the interior surface of an ear canal, inserting the wick into the ear canal wherein said insertion is accomplished with a minimum of contact between said wick and the interior surface of the ear canal, for locating said coiled wick entirely within the ear canal; hydrating said wick in situ with a liquid medicament to cause it to uncoil radially outward into substantial contact with the interior surface of the ear canal and thereby apply the medicament thereto said outer surface contacting an ear canal inner surface to apply medicament to the interior surface of the ear canal, said expanded member being characterized by an open unobstructed passage therethrough, said uncoiling causing said device to expand radially outward and defining an open, unobstructed passage through the wick, said passage extending longitudinally of said device for essentially the entire length thereof and connecting said device ends together and permitting substantially free unobstructed passage of sound waves through the wick from one end of said device to the other end thereof whereby a user's hearing is essentially unimpaired when said wick is positioned within such user's ear canal and expanded into contact with the inner surfaces of that ear canal, said material being characterized such that when hydrated while unconfined said device will expand and completely uncoil to its original flat, non-compressed dimensions.

10. A method as called for in claim 9, wherein the device outer surface contacts an ear inner surface over substantially the entire length of the device.

* * * * *